United States Patent [19]

Ryan

[11] Plant 4,261

[45] June 6, 1978

[54] IMPATIENS PLANT — CREEK

[76] Inventor: John J. Ryan, 39877 Sundale Dr., Fremont, Calif. 94538

[21] Appl. No.: 782,287

[22] Filed: Mar. 28, 1977

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

The present invention comprises a new and distinct variety of New Guinea Impatiens plant having the cultivar name Creek, discovered by me in a commercial greenhouse in Fremont, Calif.

Creek has a growth habit that is typical of a New Guinea pot variety and is similar to USDA Arabesque, and a foliage color similar to Mikkel Red Magic but is particularly characterized by bright red-green foliage that grows in richness under high light; a bright pink flower color with slightly darker eye; verses Red Magic which is dark red-rose and Arabesque which is candy-striped; a moderate flower size and average number of flowers; and the chief distinction of having good flower to foliar color contrast.

2 Drawing Figures

BACKGROUND OF THE INVENTION

The present new variety (seedling 76-2-1) was discovered by me in a commercial greenhouse in Fremont, Calif. as a result of the cross pollination of unpatented pistil parent 75-1 and unpatented pollen parent 75-6.

Asexual reproduction of my new cultivar by cuttings grown in 6" pots in a plastic (polyethylene) greenhouse in Fremont, Calif. under normal environmental conditions show that the characteristics described come true to form and are established and transmitted through succeeding propagations.

Color readings were taken during daylight hours in full sun. All colors are based on the Royal Horticultural Society Colour Chart.

BRIEF SUMMARY

Creek has a growth habit similar to USDA Arabesque and a foliage color similar to Mikkel Red Magic.

The following outstanding characteristics of Creek distinguish it from the above two varieties:

1. Its growth habit is close to USDA Arabesque; yet the stem is not as thick as Arabesque; and the variety Creek has a better breaking action.
2. The foliage is a bright red-green and grows in richness under high light. Foliage is usually darker and brighter than Red Magic.
3. Slight cupping down of leaf like Arabesque, but not flat like Red Magic.
4. Creek has a medium size, bright pink flower with a slightly darker eye; unlike the medium size, dark red-rose flower of Red Magic; or the large candy-striped flower of Arabesque.
5. It is less floriferous than Red Magic but more so than Arabesque.

DESCRIPTION OF THE PHOTOGRAPH

The accompanying colored photograph illustrates the overall appearance of the cultivar Creek showing the colors as true as is reasonably possible for this type of colored reproduction. However, under low light and cool temperatures, the flower darkens and foliage lightens. Under high light, the foliage darkens tremendously and the flower fades. The second photograph illustrates the leaf variability under different environmental conditions.

DETAILED DESCRIPTION

The following detailed description of Creek is based on observations made of the new cultivar on Jan. 13, 1977. The cultivar was grown in 6" pots in a plastic (polyethylene) greenhouse in Fremont, Calif., under environmental conditions considered normal for that time of year.

PLANT

Name: Creek.
Origin: Seedling 76-2-1 of the cross pollination of unpatented pistil parent 75-1 and unpatented pollen parent 75-6.
Height to flowering: 38 cm.
Growth: Fast.
Type of cuttings: Terminal or stem.
Rooting time: Typical, 10–14 days.
Rooting habit: Fast, dendritic.

FOLIAGE

Arrangement: Lower leaves opposite (usually only one set), upper foliage of any shoot whorls of 3–4.
Shape: Elliptic.
Tip: Acuminate.
Base: Attenuate.
Margin: Ciliate at base to serrulate at tip.
Venation: Pinnate.
Size: Petiole and blade 16 to 18 cm., length of blade 14 to 15 cm., width of blade at wides point 4 to 5 cm.
Surface:
*Smoothness.*—Occasional slight cupping down of leaf.
*Texture.*—Glabrous, typical waxy.
Variegation: None.
Color: Very variable under different light intensities.
*Petiole.*—50 B.
*Veins.*—a. 47B — upper surface, b. 50A — lower surface.
*Leaf.*—a. Upper: 1. Young leaf — 137C base overlay 47B, 2. Old Leaf — 143B. b. Lower: 1. 181A — young leaf, 2. 180A — old leaf.

STEM

Color: 145C; Stem color decreases rapidly as you go down the stem.

Internode:

*Length.*—Moderate.

*Size.*—Moderately heavy.

Node Expanded (relative to internode): Slightly expanded.

Breaking action: Good.

FLOWER

Form: Typical.

Borne: End of branches, terminal

Blooming habit:

*Relative number.*—Moderate to heavy.

*Time to flowering.*—Typical.

*Longevity.*—Typical (3-5 days), heavily dependent on temperature.

Size of mature flower: First flower on a plant may be small.

*Length.*—4.5 cm.

*Width.*—4.5 cm.

*Spur.*—5.0 to 5.5 cm.

Color: The flower color of Creek is very easily changed by light intensity from a salmon nearly matching the petal back (41C) in winter to a very light Pink if light intensity gets too high.

*Eye.*—58B.

| | |
|---|---|
| 1. Eye: | 58B |
| 2. Middle<br>3. Edge | 52C - on first reading; second reading on 10-26-77, 52 D - darker portion of flower, mostly upper petal, 50D - lower petals especially as edge is approached. |

-continued

| | |
|---|---|
| 4. Pedicel: | 142 C |

REPRODUCTIVE ORGANS

Stamen:

| | |
|---|---|
| 1. Anthers<br>2. Filaments | typical in form, fused hood over pistil |
| 3. Pollen:<br>a. Color: 158B<br>b. Abundance: typical, plenty | |

Pistils:

| | |
|---|---|
| 1. Style<br>2. Ovaries | typical in form |

OTHER CHARACTERISTICS

Diseases: Creek is no more susceptible than other Impatiens varieties to most soft rots.

Insects: Creek is more resistant to spider mites than most Impatiens varieties on the market.

I claim:

1. A new and distinct form of Impatiens plants as described and illustrated, known by the cultivar name Creek and particularly characterized by its bright red-green foliage that grows in richness under high light; bright pink flower color with slightly darker eye; moderate flower size and average number of flowers; average growth habit for a New Guinea pot variety; but the chief distinction is the good flower to foliar contrast.

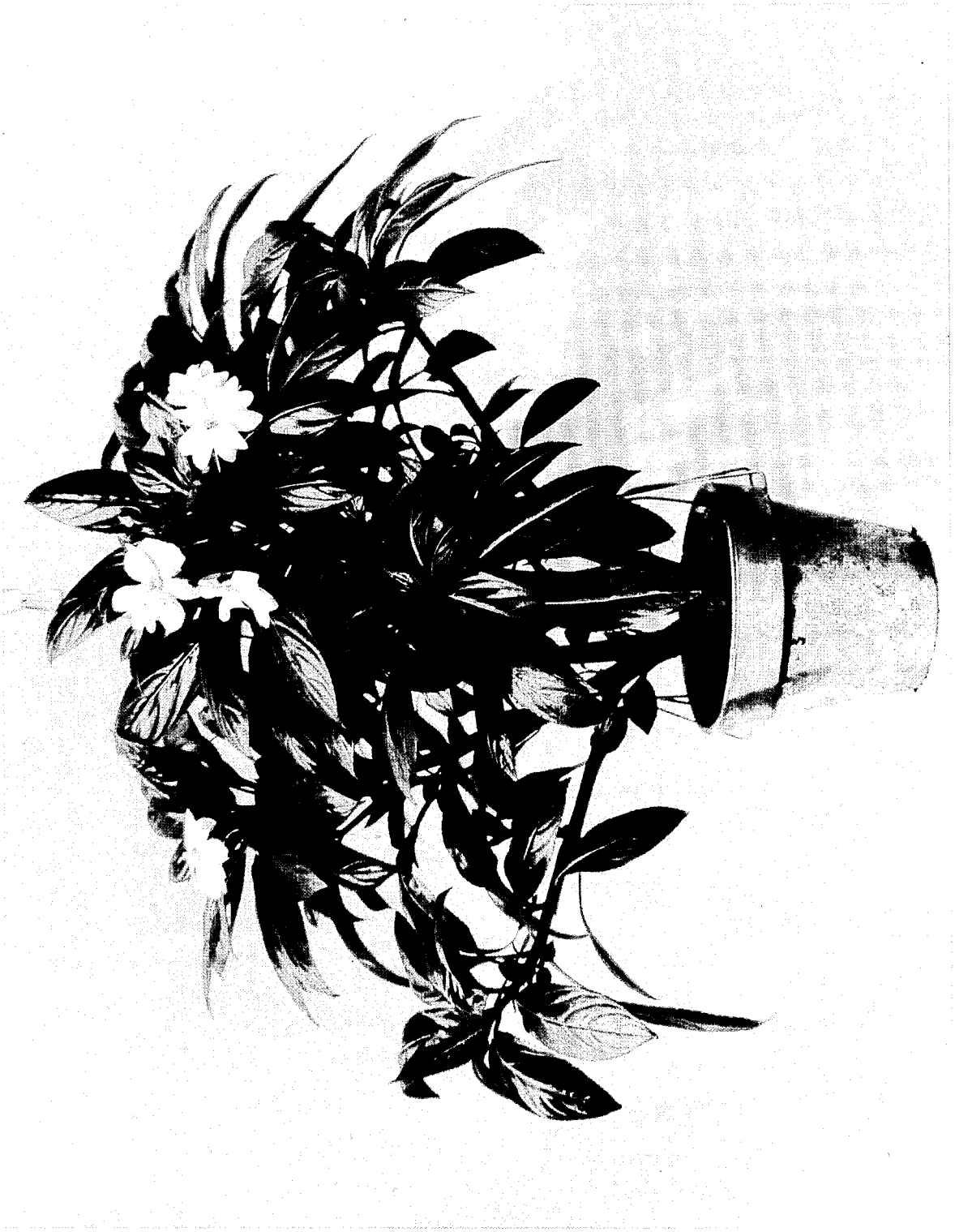

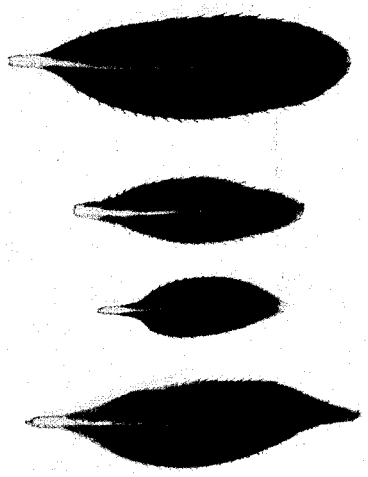

* * * * *